United States Patent [19]

Higham et al.

[11] Patent Number: 4,994,277

[45] Date of Patent: Feb. 19, 1991

[54] USE OF XANTHAN GUM FOR PREVENTING ADHESIONS

[75] Inventors: Paul A. Higham, Ringwood, N.J.; Jessica D. Posey-Dowty, Kingsport, Tenn.

[73] Assignee: Pfizer Hospital Products Group, Inc., New York, N.Y.

[21] Appl. No.: 429,891

[22] Filed: Oct. 31, 1989

[51] Int. Cl.$^5$ .......................... A61K 9/08; A61K 9/70; A61K 31/715

[52] U.S. Cl. ................................. 424/443; 424/422; 424/423; 424/426; 514/57; 604/364

[58] Field of Search ............... 424/443, 422, 423, 426; 514/57; 604/364

[56] References Cited

U.S. PATENT DOCUMENTS

| | | | |
|---|---|---|---|
| 2,040,880 | 5/1936 | Rigby | 18/54 |
| 3,632,754 | 1/1972 | Balassa | 424/180 |
| 4,378,017 | 3/1983 | Kosugi et al. | 424/35 |
| 4,407,787 | 10/1983 | Stemberger | 514/57 |
| 4,532,134 | 7/1985 | Malette | 514/55 |
| 4,572,906 | 2/1986 | Sparks | 514/21 |
| 4,603,695 | 8/1986 | Ikada et al. | 128/334 R |
| 4,659,700 | 4/1987 | Jackson | 514/55 |
| 4,713,375 | 12/1987 | Lindstrom et al. | 514/57 |
| 4,840,626 | 6/1989 | Linsky et al. | 604/364 |
| 4,886,787 | 12/1989 | de Belder et al. | 514/62 |

FOREIGN PATENT DOCUMENTS

| | | |
|---|---|---|
| 200574 | 9/1984 | European Pat. Off. . |
| WO86/00912 | 2/1986 | PCT Int'l Appl. . |
| WO87/07618 | 12/1987 | PCT Int'l Appl. . |
| 2026516 | 2/1983 | United Kingdom . |

*Primary Examiner*—Merrell C. Cashion, Jr.
*Assistant Examiner*—Amy Hulina
*Attorney, Agent, or Firm*—Peter C. Richardson; Lawrence C. Akers; Raymond W. Augustin

[57] ABSTRACT

A method for preventing adhesion utilizes a viscoelastic gel formed from xanthan gum. The gel is more viscous than blood and is soluble in aqueous solutions. The gel is placed between the tissues by a syringe. The method includes mixing the xanthan gum with either a saline solution or Tyrode's solution to form the gel.

4 Claims, No Drawings

USE OF XANTHAN GUM FOR PREVENTING ADHESIONS

FIELD OF THE INVENTION

This invention relates to an adhesion preventive. More particularly, it relates to a bio-compatible xanthan gum material which is useful in surgical operations for preventing adhesions of vital tissues such as skin, blood vessels or organs.

DESCRIPTION OF THE PRIOR ART

Vital tissues such as blood vessels or organs including kidney, liver and intestines are coated with mucous membranes or serous membranes so that they can function independently of each other. Examples of these mucous or serous membranes are the body wall pleura and organ pleura in the thoracic cavity and the parietal peritoneum and mesentery in the abdominal cavity, each protecting the corresponding organs. Surgical operations or inflammation in those portions of the body coated with serous membranes could result in adhesion regardless of the size of the affected part. Such adhesion between vital tissues may be observed not only in particular portions of the body but in all vital tissues. Adhesion between vital tissues has heretofore presented a serious problem in the surgical field.

In the field of orthopedics, conditions such as acute or chronic arthritis such as suppurative, rheumatoid arthritis, gonorrheal, tuberculous or traumatic injuries at a joint, such as fracture or sprain, would result in ankylotic diseases wherein the surfaces of the bones constituting the joint adhere to each other and thereby restrict the mobility of the joint. Congenital radioulnar synostosis wherein a spoke bone and an ulna adhere together is difficult to remedy by a surgical operation, since the separated bones would frequently re-adhere.

As described above, adhesion of vital tissues, large or small, may be observed in most surgical fields. Adhesion could occur for various reasons including mechanical and chemical stimulations of vital tissues accompanying surgical operations, postoperative bacterial infection, inflammation or complications. Consequently, it is necessary to prevent postoperative adhesion between vital tissues.

Conventional adhesion preventives such as liquid paraffin, camphor oil, chondroitin sulfate and urea exhibit an insufficient effect since they function only temporarily. On the other hand, synthetic polymer membranes such as gutta percha or poly(tetrafluoroethylene), which have been used for preventing postoperative adhesion at portions of the body where there is a fear of adhesion setting in, would remain in the body as foreign bodies. Therefore, it is necessary to take out the used membrane by re-operation.

Consequently, there has been a long felt need to find ways to prevent adhesions after surgery. Others have addressed the problem of adhesion prevention utilizing biodegradable materials. U.S. Patent 4,603,695, which issued on Aug. 5, 1986 to Ikada et al, refers to the use of an absorbable polyester polymer. This patent also mentions the use of chitin. These materials can be absorbed by hydrolysis in vivo.

Polysaccharides such as chitin and chitosan (partially de-acetylated chitin) are well known biocompatible materials whose preparation has been described in U.S. Pat. No. 2,040,880, which issued on May 19, 1936.

Uses of chitin and other polysaccharides for wound healing or adhesion prevention purposes are referred to in U.S. Pat. Nos. 3,632,754, 4,532,134, 4,659,700, 4,572,906, 4,378,017, British Patent No. 2026516, European Patent No. 0200574 and PCT publications WO 86/00912 and WO 87/07618 (PCT/US87/01246). None of these patents, however, teach the use of xanthan gum for preventing adhesions.

The adhesion prevention material of the present invention is an aqueous hydrogel polymer which dissolves over time in vital tissues. Since this material already contains water in order to obtain the desired properties, later hydrolysis is unnecessary. In the past, hydrogels have been used, but they have either been covalently cross-linked to improve their life, and therefore have undesirably long degradation times, or else they did not last long enough in the site to be effective.

The adhesion prophylaxis of the present invention comprises a polymer which is biocompatible and biodegradable comprised of polysaccharide units which may be broken down by the body into simple sugars which are then metabolized. The half life of the xanthan gum hydrogel material to be used in adhesion prevention can range from about 2-3 days to up to about one year in vivo, depending on the concentration of the xanthan gum. Therefore, it is possible to prevent adhesion by placing the adhesion preventative at that portion of the body of a warm blooded mammal undergoing surgery where there is a fear of adhesion setting in. The period the prophylaxis stays in place depends on the rate of absorption by dissolution or by degradation. The adhesion preventative made of the material of the present invention will disappear without requiring re-operation for its removal.

SUMMARY OF THE INVENTION

It is an object of this invention to provide a biodegradable, absorbable material capable of preventing adhesions.

It is another object of this invention to provide a material for prevention of adhesions which can form a viscoelastic fluid of various concentrations of xanthan gum which will begin to degrade after a predetermined time period.

It is yet an additional object of the invention to provide a material for preventing adhesions which can be made from bio-compatible material which can be easily made into a gel and can be easily and safely applied during surgery performed on humans or other mammals.

Accordingly, these and related objects are achieved by a preferred method which includes placing a material comprising a gel formed of xanthan gum, which mixture is soluble in an aqueous solution, between the tissues in order to prevent adhesions.

DESCRIPTION OF THE PREFERRED EMBODIMENTS

The biodegradable, absorbable hydrogel polymers to be used as an adhesion preventive of the present invention are polymers which revert to the gel and/or fluid state in vivo over time. Examples of these polymer materials include polysaccharide gums containing amino sugars such as xanthan gum.

Xanthan gum is an exocellular heteropolysaccharide produced by a distinct fermentation process. The bacterium *xanthomonas camoestris* generates this gum on specific organelles at the cell surface by a complex enzymatic process; the gum both encapsulates the bacterial cell and is secreted into the surrounding medium. The composition and structure of the xanthan gum produced by commercial fermentation is identical to the polysaccharide formed by *xanthomonas campestris* on plants belonging to the cabbage family, where it occurs naturally.

Each xanthan gum repeat unit contains five sugar residues: two glucose, two mannose, and one glucuronic acid. The polymer backbone consists of 1,4 linked β-D-glucose and is therefore identical in structure to cellulose. Trisaccharide side chains on alternating anhydroglucose units distinguish xanthan gum from cellulose. Each side chain comprises a glucuronic acid residue between two mannose units.

Numerous studies have indicated a molecular weight for xanthan gum of approximately two million, which corresponds to approximately two thousand repeat units per polymer molecule.

Xanthan gum solutions are highly pseudoplastic. When shear stress is increased, viscosity is progressively reduced. Upon the reduction of shear, total viscosity is recovered almost instantaneously. This behavior results from the high-molecular-weight, rod-like molecule, which forms complex molecular aggregates through hydrogen bonds and polymer entanglement.

At low concentrations xanthan gum displays the unusually high viscosities important to its suspension-stabilizing properties.

Solutions of xanthan gum at 1% or higher concentration appear almost gel-like at rest, yet these same solutions pour readily and have a very low resistance to mixing and pumping. These same qualities are observed at typical use levels of about 0.1% to 0.3%.

At or below about 0.25% gum concentration, monovalent salts such as sodium chloride cause a slight decrease in viscosity. At higher gum concentrations, viscosity increases with added salt. At a monovalent salt level of 0.1%, the viscosity plateau is reached, and further addition of salt has no effect on viscosity. Many divalent metal salts, including those of calcium and magnesium, have a similar impact on viscosity.

A synergistic interaction occurs between xanthan gum and galactomannans such as guar gum, locust bean gum, and cassia gum. This interaction results in enhanced viscosity or gelation.

Among these materials, it is preferable to use water soluble polymers which have not been covalently cross-linked to form insoluble materials. It has been found advantageous to use those polymers which either can be used underivatized as visco-elastic materials or which can form substances which will begin to degrade in a period of about 2-5 days up to about 1 year. In order to vary the degradation time, the viscosity of the gel can be varied by varying the concentration of the xanthan gum. The more viscous the gel, the longer the degradation time.

It is possible to prevent adhesions by injecting a visco-elastic material such as a gel of xanthan gum, which is more viscous and elastic than blood, so that it prevents blood from clotting at the interface of two vital tissues, thus preventing an adhesion from forming.

The invention will now be described in further detail with reference being made to the following examples. It should, however, be recognized that the examples are given as being illustrative of the present invention and are not intended to define the spirit and scope thereof.

EXAMPLE 1

Xanthan gum gels were formed by mixing between 1.0 and 3.0 grams of Kelco xanthan gum with 100 grams of Tyrode's solution using a high speed mixer. The resultant solutions were a thick viscoelastic fluid which could be heat sterilized and placed in a syringe for easy application during surgery.

EXAMPLE 2

Xanthan gum gels were formed by mixing between 1.0 and 3.0 grams of Kelco xanthan gum with 100 grams of 0.9% saline solution (pH 7) using a high speed mixer. When 1.0 to 3.0 grams of Kelco xanthan gum was mixed with 100 grams of 0.9% saline solution (pH 7) using a high speed mixer, as above, a viscoelastic material resulted. Again, this material could easily be injected between tissues to prevent adhesions.

While several examples of the present invention have been described, it is obvious that many changes and modifications may be made thereunto, without departing from the spirit and scope of the invention.

We claim:

1. A method of preventing adhesions between vital tissues comprising the step of placing a viscoelastic gel comprising 1-3 weight percent biodegradable xanthan gum in an aqueous solution, between the tissues.

2. The method as set forth in claim 1 further comprising the step of mixing an anti-thrombogenic agent with the biodegradable xanthan gum solution prior to placing the material between the tissues.

3. The method as set forth in claim 1 wherein the viscoelastic gel comprises between 1 and 3 grams of xanthan gum dissolved in a 0.9% saline solution at a pH of 7.

4. The method as set forth in claim 1 wherein the viscoelastic gel comprises between 1 and 3 grams of xanthan gum mixed with 100 grams of Tyrode's solution.

* * * * *